US011894113B2

(12) United States Patent
Helton et al.

(10) Patent No.: US 11,894,113 B2
(45) Date of Patent: Feb. 6, 2024

(54) ONTOLOGICAL STANDARDS BASED APPROACH TO CHARTING UTILIZING A GENERIC CONCEPT CONTENT BASED FRAMEWORK ACROSS MULTIPLE LOCALIZED PROPRIETARY DOMAINS

(71) Applicant: CERNER INNOVATION, INC., Kansas City, KS (US)

(72) Inventors: Rob Helton, Shawnee, KS (US); Cameron Travers, Overland Park, KS (US); Matthew Birkel, Mission, KS (US); Mark Davenport, Lenexa, KS (US); Patrick Shine, Fairway, KS (US); Nick Kroeker, Centennial, CO (US); Joel Isernhagen, Overland Park, KS (US); Anna Terranella, Kansas City, MO (US); Marissa Brooks, Washington, DC (US)

(73) Assignee: Cerner Innovation, Inc., Kansas City, MO (US)

( * ) Notice: Subject to any disclaimer, the term of this patent is extended or adjusted under 35 U.S.C. 154(b) by 0 days.

(21) Appl. No.: 16/237,136

(22) Filed: Dec. 31, 2018

(65) Prior Publication Data
US 2020/0211684 A1   Jul. 2, 2020

(51) Int. Cl.
*G16H 15/00* (2018.01)
*G16H 10/60* (2018.01)
(Continued)

(52) U.S. Cl.
CPC .............. *G16H 15/00* (2018.01); *G06N 3/08* (2013.01); *G06Q 10/0633* (2013.01); *G06Q 10/06393* (2013.01); *G16H 10/60* (2018.01)

(58) Field of Classification Search
CPC .......... G16H 10/60; G16H 15/00; G06N 3/08; G06Q 10/0633; G06Q 10/06393
See application file for complete search history.

(56) References Cited

U.S. PATENT DOCUMENTS

| 8,195,594 | B1 * | 6/2012 | Bryce | G16H 15/00 706/47 |
| 2002/0120435 | A1 * | 8/2002 | Frazier | G06N 3/105 704/1 |

(Continued)

FOREIGN PATENT DOCUMENTS

WO   WO-2009008968 A1 *   1/2009   ........... G06F 19/322

*Primary Examiner* — Mamon Obeid
*Assistant Examiner* — Chance L Smith
(74) *Attorney, Agent, or Firm* — Invoke

(57) ABSTRACT

Embodiments of the present disclosure provide a cloud-based integrated charting system that utilizes a universal mapping service across services and clients to provide insights for the provider into customizations made by clients. Additionally, the system provides content building tools that enable clients to customize content to update models provided by the provider. A mapping service maps model codes corresponding to model concepts to a plurality of standard based concept codes corresponding to client domain specific customized concepts for an ontology of the one or more ontologies. A workflow recommendation is provided that enables a user to chart data and includes the model concepts comprising charting elements. Accordingly, the data is stored in a client database in accordance with the client domain specific customized concepts. Since the model concepts are mapped to the client domain specific customized concepts, the workflow recommendation can be pre-populated with data from the client database.

15 Claims, 9 Drawing Sheets

(51) Int. Cl.
  *G06Q 10/0639* (2023.01)
  *G06N 3/08* (2023.01)
  *G06Q 10/0633* (2023.01)

(56) References Cited

U.S. PATENT DOCUMENTS

| | | | | |
|---|---|---|---|---|
| 2004/0153338 A1* | 8/2004 | Kim | ............... | G06Q 50/22 |
| | | | | 705/2 |
| 2004/0189718 A1* | 9/2004 | Stein | ............... | G06Q 10/10 |
| | | | | 715/853 |
| 2005/0149536 A1* | 7/2005 | Wildes | ............... | G06F 8/20 |
| 2007/0143149 A1* | 6/2007 | Buttner | ............... | G06Q 50/24 |
| | | | | 705/3 |
| 2008/0208619 A1* | 8/2008 | Swanson | ............... | G06Q 10/06375 |
| | | | | 705/2 |
| 2010/0049740 A1* | 2/2010 | Iwase | ............... | G16H 10/60 |
| | | | | 705/7.27 |
| 2010/0274580 A1* | 10/2010 | Crownover | ............... | G06Q 50/22 |
| | | | | 705/2 |
| 2011/0270630 A1* | 11/2011 | Green, III | ............... | G06Q 10/10 |
| | | | | 705/3 |
| 2013/0030827 A1* | 1/2013 | Snyder | ............... | G06F 19/324 |
| | | | | 705/2 |
| 2014/0095203 A1* | 4/2014 | Anand | ............... | G06Q 50/24 |
| | | | | 705/3 |
| 2014/0278549 A1* | 9/2014 | Fritsch | ............... | G16H 10/60 |
| | | | | 705/3 |
| 2014/0372965 A1* | 12/2014 | Alibakhsh | ............... | G06Q 10/103 |
| | | | | 717/101 |
| 2015/0112700 A1* | 4/2015 | Sublett | ............... | G06Q 30/0201 |
| | | | | 705/2 |
| 2017/0116169 A1* | 4/2017 | Malek | ............... | H04L 67/10 |
| 2017/0300634 A1* | 10/2017 | Chiang | ............... | G16H 10/60 |

* cited by examiner

ONTOLOGICAL STANDARDS BASED APPROACH TO CHARTING UTILIZING A GENERIC CONCEPT CONTENT BASED FRAMEWORK ACROSS MULTIPLE LOCALIZED PROPRIETARY DOMAINS

BACKGROUND

Managing content for a provider of health care information technology services is an extremely difficult and time consuming task. After the content is initially developed by the provider, each individual client may utilize and customize the content in a variety of formats and with a variety of naming conventions. As the customizations are local to the client installations (i.e., only made in the domain of the client), they are largely unknown by the provider.

This results in a disconnect between the content utilized by each client and the content initially developed by the provider. Moreover, if updates to the initial content is warranted, some clients may not adopt the updated content because of the disconnect between the updated content in the domain of the provider and the customized content in the domain of the client.

Currently, some providers create unique identifiers for each individual client so that the initial content (or updated content) can be mapped to the customized content. Unfortunately, this mapping is limited to the provider and the customization to the individual service being utilized by the client. In other words, each client may utilize multiple services provided by the provider and may customize content for each service differently. Thus, even if the provider is aware of the customizations, multiple mappings may be needed for each client and the process must be repeated across each client domain, resulting in a very costly and time-consuming, manual process.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to systems, methods, and user interfaces for providing a content building and mapping service. More particularly, embodiments of the present disclosure provide a cloud-based integrated charting system that utilizes a universal mapping service across services and clients to provide insights for the provider into customizations made by clients. Additionally, the cloud-based integrated charting system provides content building tools that enable clients to customize content that can be utilized to update models provided by the provider.

To do so, a model database for one or more ontologies is provided that is accessible by clients of the provider. The model database has access to a centralized concept mapping service that maps model codes corresponding to model concepts to a plurality of standard based concept codes corresponding to client domain specific customized concepts for an ontology of the one or more ontologies. When a request is received from a user of the client via a device, the client corresponding to the user and the ontology corresponding to the request can be identified. Access can then be provided to the user via the device to a workflow recommendation. The workflow recommendation enables the user to chart data for the patient and includes the model concepts provided by the provider. The model concepts may include charting elements that make up a form the clinician might utilize while charting data. As data is received, the data is stored in a client database in accordance with the client domain specific customized concepts.

In embodiments, the user can modify the workflow recommendation by modifying the model concepts. These modifications can be learned by the cloud-based integrated charting system, utilizing machine learning techniques and/or key performance indicator (KPI) data, and later shared with other clients. Additionally, because the model concepts are mapped to the client domain specific customized concepts, the workflow recommendation can be prepopulated with data from the client database.

BRIEF DESCRIPTION OF THE SEVERAL VIEWS OF THE DRAWINGS

The patent or application file contains at least one drawing executed in color. The present invention is described in detail below with reference to the attached drawing figures, wherein:

FIG. 7 depicts an illustrative screen display of a pre-established base charting view with prepopulated data wherein the reference data context is supplied from a central library with multiple illustrative implementation of the front-end user experience, in accordance with embodiments of the present invention;

DETAILED DESCRIPTION

Figure 1:
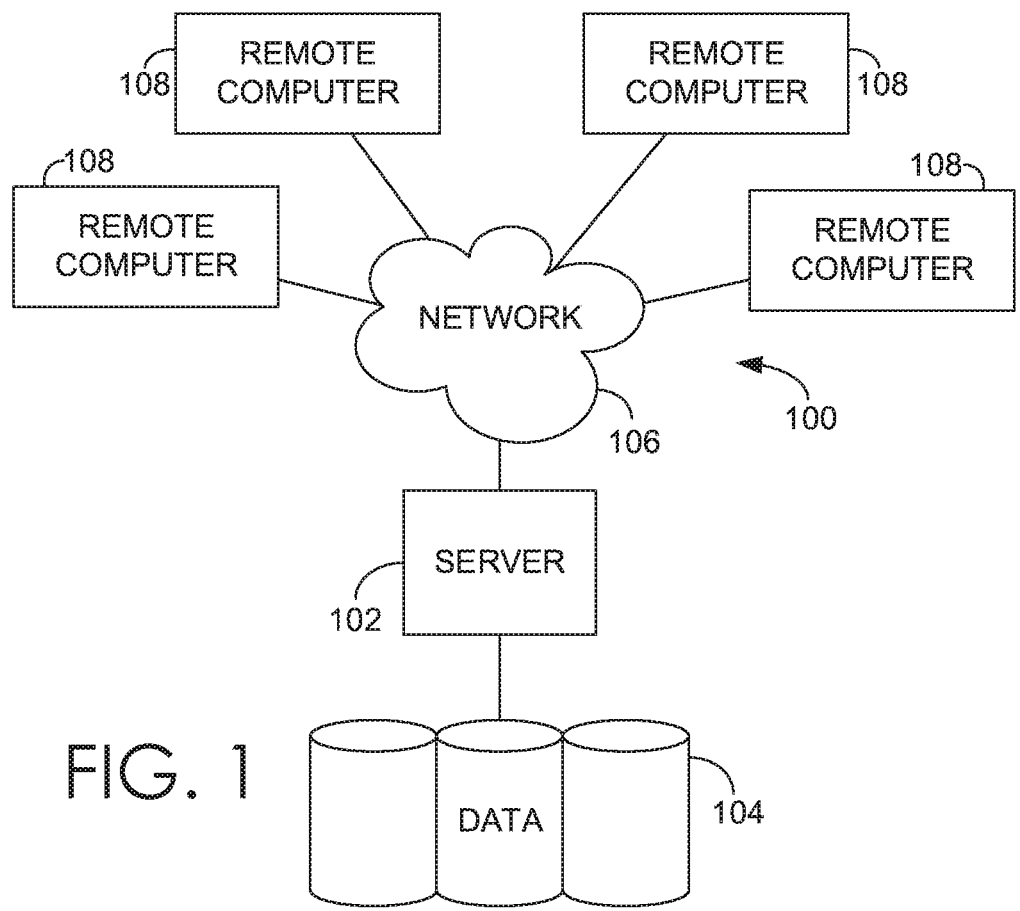
FIG. 1 is a block diagram of an exemplary operating environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

As noted in the background, in the context of content (e.g., charting forms) initially developed by providers, customizations made by clients are largely unknown by the provider. The resulting disconnect between content utilized by each client and the content initially developed by the provider causes several problems. First, if updates to the initial content is warranted (e.g., a new field to a charting form is needed due to a change in guidelines), some clients may not adopt the updated content because of the effort required to reconcile the disconnect.

To overcome this, some providers create unique identifiers for each individual client so the initial content (or updated content) can be mapped to the customized content. However, this mapping is limited to the provider and the customization to the individual service being utilized by the client. Because each client may utilize multiple services provided by the provider and may customize content for each service differently, mappings must be made for each service utilized by the client. Thus, even if the provider is aware of the customizations, the reconciliation process is a very costly and time-consuming, manual process. Moreover, the process must be repeated across each client domain.

For example, a provider may develop content (e.g., a charting form comprising elements or model concepts) that identifies a model concept (e.g., heart rate) with a numerical identifier of 123 (i.e., a model code). This form may be released to all clients. As the clients implement the charting form locally, one client may already be utilizing a numerical identifier of 123 for some other locally customized content (e.g., a client concept that is different than heart rate). So, for that client's local implementation, the client may utilize a different numerical identifier (e.g., 234) for heart rate on that charting form. Once that has occurred, the provider no longer has insight into how the client is utilizing the charting form, or customizing the charting form (e.g., modifying a field type, adding or removing fields, and the like) because customizations are made locally.

Even if the client utilizes the same numerical identifier but customizes the charting form in a different way (e.g., modifying a field type, adding or removing fields, and the like), the provider may not be able to utilize the client data to prepopulate other forms the client uses. For example, if the client changes the field for a heart rate to a text field instead of a numerical field, the provider is no longer able to process the data that is entered and cannot use the data to prepopulate other forms for the client that also might utilize heart rate.

If the client utilizes the charting form for multiple services provided by the provider, and utilizes different numerical identifiers (e.g., 234, 345, 456) for a particular concept code for each of the services, the problem is even further exacerbated. For example, if the provider later makes a modification to the original charting form (e.g., modifying a field type, adding or removing fields, and the like) due to a change in guidelines, that change must be propagated to each instance of the form utilized by the client. Since each of the instances are assigned different numerical identifiers, the reconciliation process becomes increasingly difficult, time-consuming, and costly.

Embodiments of the present disclosure relate to systems, methods, and user interfaces for providing a content building and mapping service. More particularly, embodiments of the present disclosure provide a cloud-based integrated charting system that utilizes a universal mapping service across services and clients to provide insights for the provider into customizations made by clients. Additionally, the cloud-based integrated charting system provides content building tools that enable clients to customize content that can be utilized to update models provided by the provider.

To do so, a model database for one or more ontologies is provided that is accessible by clients of the provider. The model database has access to a centralized concept mapping service that maps model codes corresponding to model concepts to a plurality of standard based concept codes corresponding to client domain specific customized concepts for an ontology of the one or more ontologies. When a request is received from a user of the client via a device, the client corresponding to the user and the ontology corresponding to the request can be identified. Access can then be provided to the user via the device to a workflow recommendation. The workflow recommendation enables the user to chart data for the patient and includes the model concepts provided by the provider. The model concepts may include charting elements that make up a form the clinician might utilize while charting data. As data is received, the data is stored in a client database in accordance with the client domain specific customized concepts.

In embodiments, the user can modify the workflow recommendation by modifying the model concepts. These modifications can be learned by the cloud-based integrated charting system, utilizing machine learning techniques and/or key performance indicator (KPI) data, and later shared with other clients. Additionally, because the model concepts are mapped to the client domain specific customized concepts, the workflow recommendation can be prepopulated with data from the client database.

Accordingly, one embodiment of the present disclosure is directed to one or more computer storage media having computer-executable instructions embodied thereon that, when executed by a computer, causes the computer to perform operations for managing workflow recommendations across a plurality of clients. The operations include providing a model database for one or more ontologies that is accessible by a plurality of clients. The model database has access to a centralized concept mapping service that maps a plurality of model codes corresponding to model concepts to a plurality of standard based concept codes corresponding to client domain specific customized concepts for an ontology of the one or more ontologies. The operations also include, upon receiving a request from a user of the plurality of clients via a device, identifying the client corresponding to the user and the ontology corresponding to the request. The operations further include providing access to the user via the device to a workflow recommendation that enables the user to chart data for a patient. The workflow recommendation includes the model concepts. The operations also include receiving data from the user via the device. The data is stored in a client database in accordance with the client domain specific customized concepts.

In another embodiment, the present disclosure directed to a computerized method for determining key performance indicator (KPI) data for workflow usage across a plurality of clients. The method comprises providing a model database for one or more ontologies that is accessible by a plurality of clients. The model database has access to a centralized concept mapping service that maps a plurality of model codes corresponding to model concepts to a plurality of standard based concept codes corresponding to client domain specific customized concepts for an ontology of the one or more ontologies. The method also comprises providing access to a user of the plurality of clients via a device to a workflow recommendation that enables the user to chart data for a patient. The workflow recommendation includes the model concepts. The method further comprises enabling the user to modify the workflow recommendation to generate a specific workflow recommendation by modifying the model concepts that are included in the workflow recommendation. The method also comprises measuring optimal workflow usage inside the workflow recommendation and across applications utilizing the workflow recommendation. The method further comprises comparing the workflow usage to the actual workflow usage to determine KPI data. The KPI data is stored in a KPI database and being utilized to modify the workflow recommendation.

In yet another embodiment, the present disclosure is directed to a system for managing workflow recommendations across a plurality of clients. The system comprises a processor; and a computer storage medium storing computer-usable instructions that, when used by the processor, cause the processor to: provide a model database for one or more ontologies that is accessible by a plurality of clients, the model database having access to a centralized concept mapping service that maps a plurality of model codes corresponding to model concepts to a plurality of standard based concept codes corresponding to client domain specific customized concepts for an ontology of the one or more ontologies; upon receiving a request from a user of the plurality of clients via a device, identify the client corresponding to the user and the ontology corresponding to the request; providing access to the user via the device to a workflow recommendation that enables the user to chart data for a patient, the workflow recommendation including the model concepts; and receiving data from the user via the device, the data being stored in a client database in accordance with the client domain specific customized concepts.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100.

Example operating environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Computer storage media does not comprise signals per se. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. In some embodiments, data cluster 104 takes the form of a cloud-based data store, and in some embodiments is accessible by a cloud-based computing platform.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

In some embodiments, control server 102 is a computing system or platform made up of one or more computing devices. Embodiments of control server 102 may be a distributed computing system, a centralized computing system, a single computer such as a desktop or laptop computer or a networked computing system. Thus, in some embodiments, control server 102 comprises a multi-agent computer system with software agents.

Figure 2:
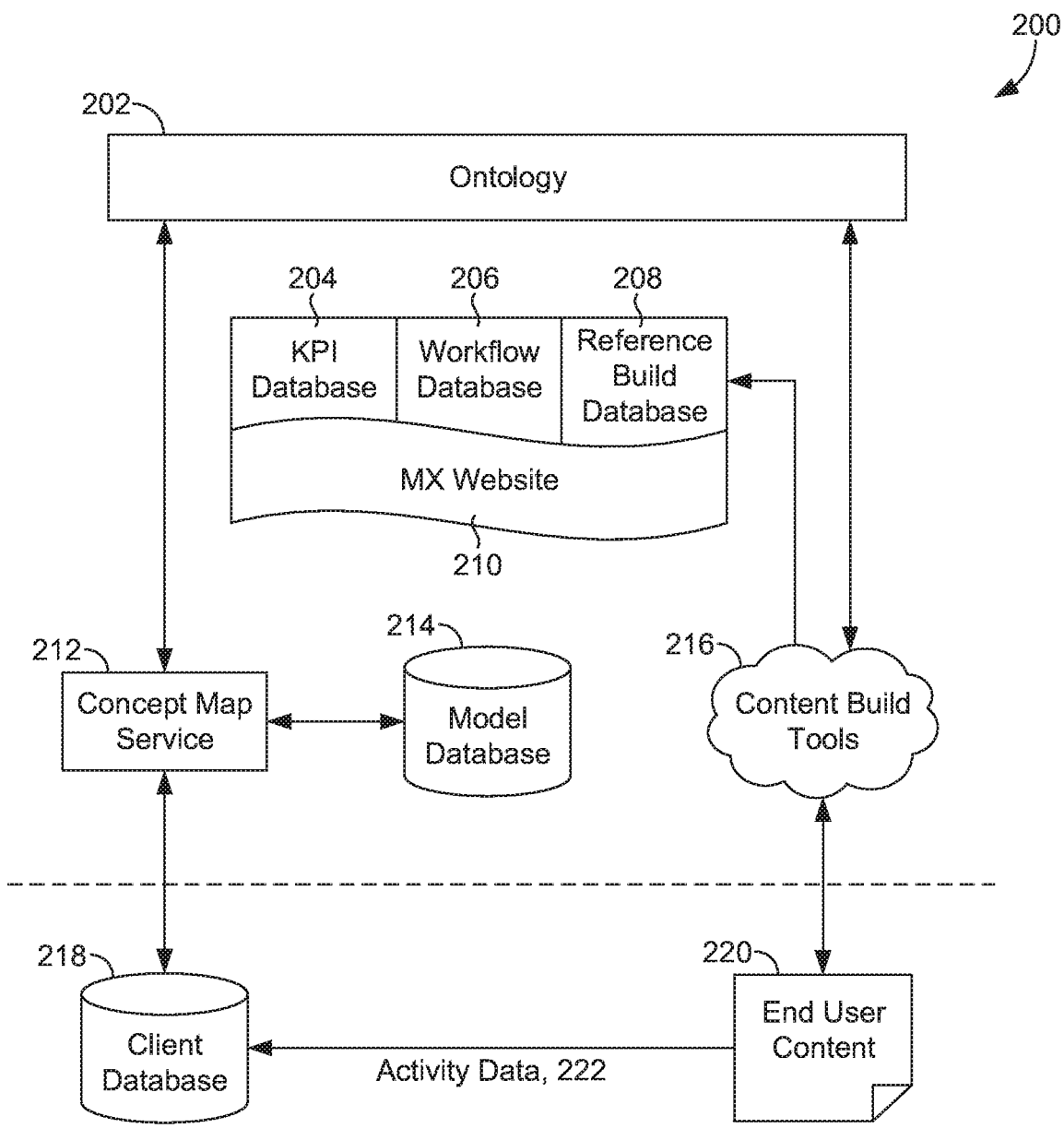
FIG. 2 depicts an exemplary framework of a cloud-based integrated charting system suitable to implement embodiments of the present invention.

Turning now to FIG. 2, an exemplary framework of a cloud-based integrated charting system 200 is shown, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The cloud-based integrated charting system 200 may be implemented via any type of computing device, such as computing device 100 described above with reference to FIG. 1, for example.

The cloud-based integrated charting system 200 generally operates to provide a content building and mapping service. More particularly, embodiments of the present disclosure provide a cloud-based integrated charting system 200 that utilizes a universal mapping service across services and clients to provide insights for the provider into customizations made by clients. Additionally, the cloud-based integrated charting system 200 provides content building tools that enable clients to customize content that can be utilized to update models provided by the provider.

To do so, a model database for one or more ontologies is provided that is accessible by clients of the provider. The model database has access to a centralized concept mapping service that maps model codes corresponding to model concepts to a plurality of standard based concept codes corresponding to client domain specific customized concepts for an ontology of the one or more ontologies. When a request is received from a user of the client via a device, the client corresponding to the user and the ontology corresponding to the request can be identified. Access can then be provided to the user via the device to a workflow recommendation. The workflow recommendation enables the user to chart data for the patient and includes the model concepts provided by the provider. The model concepts may include charting elements that make up a form the clinician might utilize while charting data. As data is received, the data is stored in a client database in accordance with the client domain specific customized concepts.

In embodiments, the user can modify the workflow recommendation by modifying the model concepts. These modifications can be learned by the cloud-based integrated charting system, utilizing machine learning techniques and/or KPI data, and later shared with other clients. Additionally, because the model concepts are mapped to the client domain specific customized concepts, the workflow recommendation can be prepopulated with data from the client database.

As shown in FIG. 2, the cloud-based integrated charting system 200 includes for an ontology 202, among other components not shown, KPI database 204, workflow database 206, reference build database 208, a user interface 210, concept map service 212, model database 214, content build tools 216, client database 218, activity data 222, and end user content 220. It should be understood that the cloud-based integrated charting system 200 shown in FIG. 2 is an example of one suitable computing system architecture. Each of the components shown in FIG. 2 may be implemented via any type of computing device, such as computing device 100 described with reference to FIG. 1, for example.

The components may communicate with each other via a network, which may include, without limitation, one or more local area networks (LANs) and/or wide area networks (WANs). Such networking environments are commonplace in offices, enterprise-wide computer networks, intranets, and the Internet. It should be understood that any number of KPI databases, workflow databases, reference build databases 208, concept map services, model databases, content build tools, and client databases may be employed within the cloud-based integrated charting system 200 within the scope of the present disclosure. Each may comprise a single device or multiple devices cooperating in a distributed environment. For instance, the concept map service 212 and/or the model database 214 may be provided via multiple devices arranged in a distributed environment that collectively provide the functionality described herein. In other embodiments, a single device may provide the functionality of multiple components of the cloud-based integrated charting system 200. For example, a single device may provide the concept map service 212 and the model database 214. Additionally, other components not shown may also be included within the network environment.

Generally, concept map service 212 provides a central lookup service for the cloud-based integrated charting system 200. To do so, the concept map service 212 maps a plurality of model codes corresponding to model concepts to a plurality of standard based concept codes corresponding to client domain specific customized concepts for an ontology of the one or more ontologies. This enables the provider to keep track of the content being used and how it is being used across all client domains for all ontologies.

The model database 214 generally stores content (e.g., charting forms) that comprise various charting elements. For example, the model concepts may comprise charting elements for a workflow recommendation (i.e., the charting form) that enables the user to chart data for the patient. The charting elements may be questions (e.g., heart rate) or definitions of the questions (e.g. a field type for the heart rate). A charting section includes a cluster of charting elements. A charting view (i.e., the workflow recommendation) is a cluster of charting sections. In this way, the model concepts are components of a form a clinician might utilize while charting data.

The client database 218 stores activity data 222 that comprise answers to the charting elements. For example, as the user charts data to answer the charting elements, the data (e.g., the end user content 220) is stored as activity data 222 in the client database 218. In some embodiments, the data is received from medical devices and is stored in the client database 218 upon confirmation from the user. In some embodiments, previous data that is stored in the client database 218 is accessed as a workflow recommendation is provided to the user and populates charting elements in the workflow recommendation. In this way, the user is able to see a history of data for the patient for a particular charting element.

Upon receiving a request from a user, via a user interface 210, to access content build tools 216, the client corresponding to the user and the ontology corresponding to the request is identified. Access to the user is provided to a workflow recommendation that may include charting elements in accordance with guidelines for the particular ontology. The user may make various changes to the workflow recommendation to create a specific workflow recommendation, such as by adding or subtracting fields, modifying field types, and the like. These changes may be stored in reference build database 208. Additionally, concept map service 212 maps model codes corresponding changes made to the model concepts to standard based concept codes corresponding to client domain specific customized concepts.

As the user begins to use the specific workflow recommendation, actual workflow usage inside the specific workflow recommendation and across applications utilizing the specific workflow recommendation can be measured. The actual workflow usage may be stored in the reference build database 208. Optimal workflow usage inside the workflow recommendation (e.g., from clients using the unmodified workflow recommendation) and across applications utilizing the workflow recommendation may be measured and stored in workflow database 206. By comparing the workflow usage to the actual workflow usage, KPI data can be determined and stored in KPI database 204. The KPI data can be used to modify the workflow recommendation if it indicates particular concepts of the specific workflow recommendation are more efficient or more utilized than particular concepts of the workflow recommendation.

Figure 3:
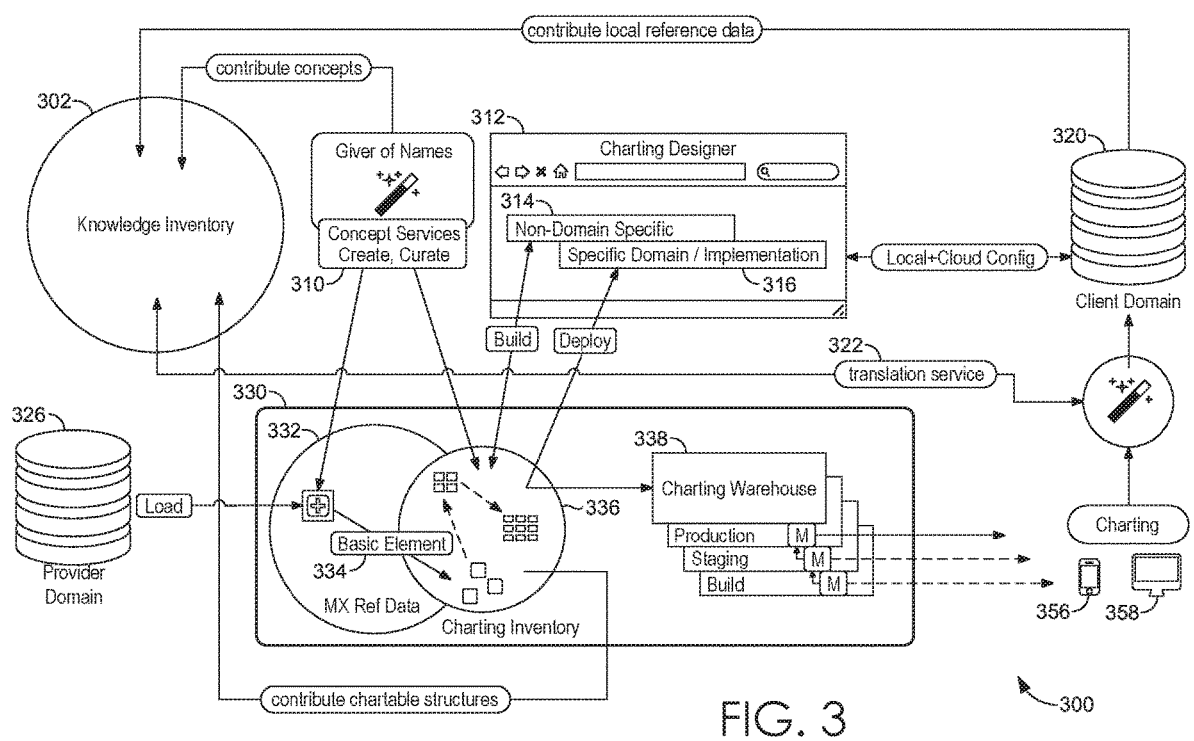
FIG. 3 depicts an exemplary framework of an integrated charting implementation of the cloud-based integrated charting system suitable to implement embodiments of the present invention.

Turning now to FIG. 3, an exemplary framework of an integrated charting implementation of the cloud-based integrated charting system 300, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The system 300 may be implemented via any type of computing device, such as computing device 100 described above with reference to FIG. 1, for example.

The charting system 300 generally operates to provide a content building and mapping service. More particularly, the system 300 provides content building tools that enable clients to customize content that can be utilized to update models provided by the provider. As shown in FIG. 3, the system 300 includes, among other components not shown, knowledge inventory 302, concept services 310, charting designer 312, local database 320, model database 326, charting inventory 330, and user devices 356, 358. It should be understood that the system 300 shown in FIG. 3 is an example of one suitable computing system architecture. Each of the components shown in FIG. 3 may be implemented via any type of computing device, such as computing device 100 described with reference to FIG. 1, for example.

The components may communicate with each other via a network, which may include, without limitation, one or more local area networks (LANs) and/or wide area networks (WANs). Such networking environments are commonplace in offices, enterprise-wide computer networks, intranets, and the Internet. It should be understood that any number of knowledge inventories, charting designers, client databases, model databases, charting inventories, or user devices may be employed within the system 300 within the scope of the present disclosure. Each may comprise a single device or multiple devices cooperating in a distributed environment. For instance, the knowledge inventory and the charting inventory may be provided via multiple devices arranged in a distributed environment that collectively provide the functionality described herein. In other embodiments, a single device may provide the functionality of multiple components of the system 300. For example, a single device may provide the knowledge inventory and the charting inventory. Additionally, other components not shown may also be included within the network environment.

Generally, the knowledge inventory includes chartable concepts (i.e., model concepts) and client domain specific customized concepts that are accessible by the system 300 to assist in chart building and deploying. Concept services 310 enable the provider to create and curate various model concepts that can be reconciled with the client domain specific customized concepts by translation service 322.

After the model concepts have been created, a client may access charting designer 312 to customize a workflow recommendation. The model concepts may be provided by model database and communicated to charting inventory 320. Charting elements 332 (e.g., basic element 334) and chartable structures 336 may be initially utilized to build a non-domain specific chart 314 (i.e., workflow recommendation). Any changes or modifications made to the non-domain specific chart 314 create a specific domain implementation 316 (i.e., specific workflow recommendation). To do so local and cloud configuration data may be provided by client database 320 to charting designer 312.

The resulting workflow recommendation may be stored in charting warehouse 338 and communicated to user devices 356, 358 at the time of charting. As the client charts data, translation service 322 translates the client concept code into the corresponding model concept code so data can be provided to knowledge inventory 302. This data may include data corresponding to how the user actually utilizes the chart. Additionally, data is provided to the client database 320 that includes activity data corresponding to patient-specific entries made by the user during the charting process.

Figure 4:
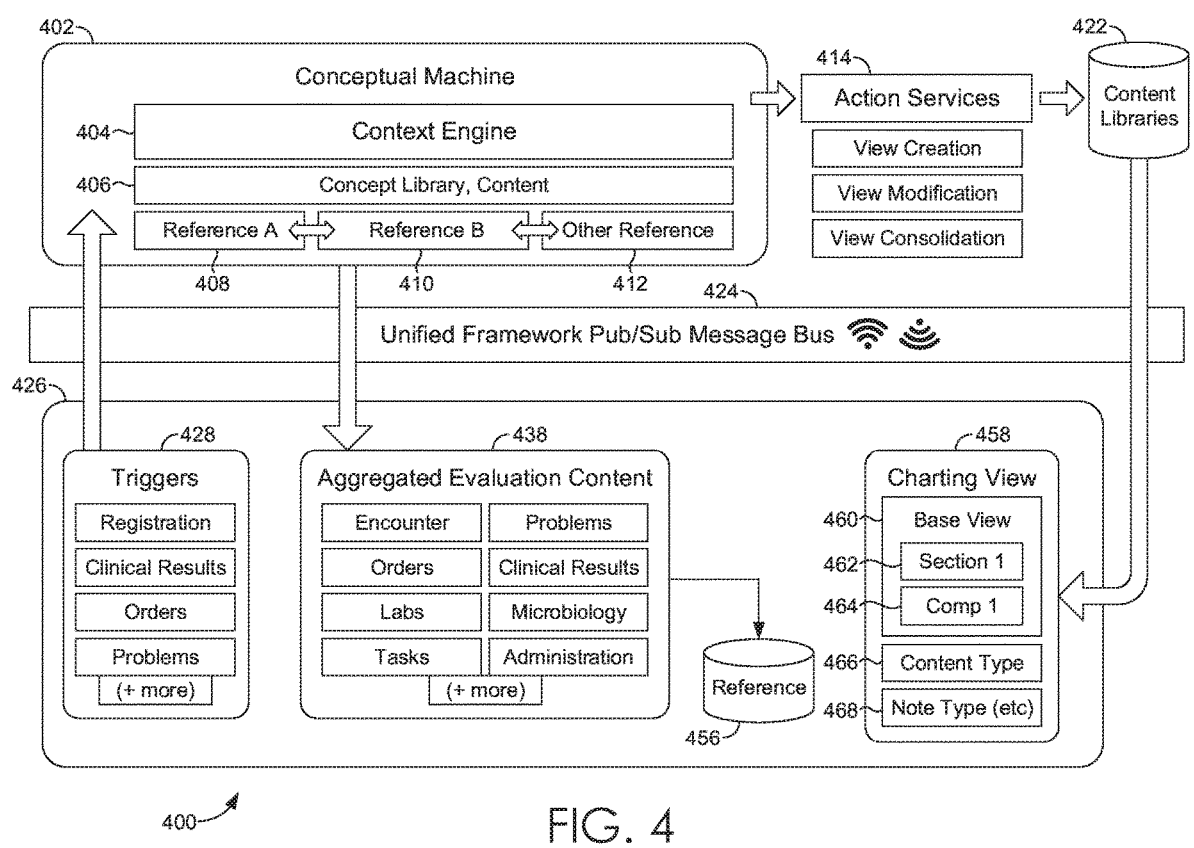
FIG. 4 depicts an exemplary framework of an integrated charting dependent implementation of contextual learning and triggers based on demographics and other patient/facility/organization specific data sets that feed into the cloud-based integrated charting system suitable to implement embodiments of the present invention.

In FIG. 4, an exemplary framework of an integrated charting implementation of the cloud-based integrated charting system 400 is provided, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The system 400 may be implemented via any type of computing device, such as computing device 100 described above with reference to FIG. 1, for example.

The system 400 generally operates to provide a content building and mapping service. More particularly, the system 400 provides a framework that enable a charting view to be provided to a client in a view consistent with preferences of the client. As shown in FIG. 4, the system 400 includes, among other components not shown, conceptual machine 402, action services 414, content libraries 422, triggers 428, aggregated evaluation content 438, reference database 456, and charting view 458, all in communication with each other via a message bus 424. It should be understood that the system 400 shown in FIG. 4 is an example of one suitable computing system architecture. Each of the components shown in FIG. 4 may be implemented via any type of computing device, such as computing device 100 described with reference to FIG. 1, for example.

It should be understood that any number of conceptual machines, action services, content libraries, triggers, aggregated evaluation content, reference databases, and charting views may be employed within the system 400 within the scope of the present disclosure. Each may comprise a single device or multiple devices cooperating in a distributed environment. For instance, the conceptual machine and action services may be provided via multiple devices arranged in a distributed environment that collectively provide the functionality described herein. In other embodiments, a single device may provide the functionality of multiple components of the system 400. For example, a single device may provide the conceptual machine and action services. Additionally, other components not shown may also be included within the environment.

Generally, the conceptual machine 402 provides the appropriate workflow recommendation to the user at the appropriate time. A context engine 404 may receive various triggers 428 (e.g., registration of a patient, clincial results, orders, problems, and the like) from the client domain 426. Concept library 406 identifies the appropriate model concepts to include in the workflow recommendation. Reference data from various sources Reference A 408, Reference B 410, or Other Reference 412 may be utilized to prepopulate the workflow recommendation with aggregated evaluation content 438 (i.e., previous data) for the patient. The previous data may include encounter information, orders, labs, tasks, problems, clinical results, microbiology information, administration data, and the like. The previous data may be stored in reference database 456.

Action services 414 receives the workflow recommendation and applies any actions (e.g., creation modification, consolidation) utilizing the content libraries 422 to provide the charting view 458. The charting view 458 includes a base view 460, base section(s) 462, charting element(s) 464, and may include structure information such as content type 466 or note type 468.

In practice, a clinician may walk into a patient room and, utilizing a handheld device, open a chart on the device. The chart may initially open into a summary mode and may include previous values of the vitals. To provide the previous vitals, the application on the device may request from a cloud service (i.e., the cloud-based integrated charting system) previous values corresponding to the currently open chart. Since the model codes of the currently open chart are mapped to client codes for a particular ontology, the cloud service is able to request data corresponding to the current encounter and may do so from multiple clients.

In some embodiments, the cloud-based integrated charting system identifies a list of vital signs and structure associated with the chart (e.g., the charting elements) that are relevant to the context (e.g., the system learns that every four hours a particular clinical enters a room to chart vitals). In this example, the particular chart (i.e., the workflow recommendation) corresponds to vitals. The elements in the chart correspond to particular model codes that have been defined across all clients. The system can then, utilizing client codes, request previous data to populate the chart with the most recent data corresponding to the encounter for the selected ontology. The client codes enable the data to be client-specific when providing the most recent data to provide additional context for the clinician.

The process of determining what to chart is similar to the process of actually charting, as described above. Continuing the vitals example, a clinician may request from the system what vital measurements are available to chart. The system requests, from a model database, the available vital measurements (e.g., the model concepts). The clinician can make changes (additions or subtractions) to the chart and the model codes corresponding to each of these charting elements is mapped to client codes. Thus, when a clinician charts data for each of the vital measurements, the data can be stored properly in the local client environment and include the proper context so if the data is later retrieved by the system it can be provided with context.

Figure 5:
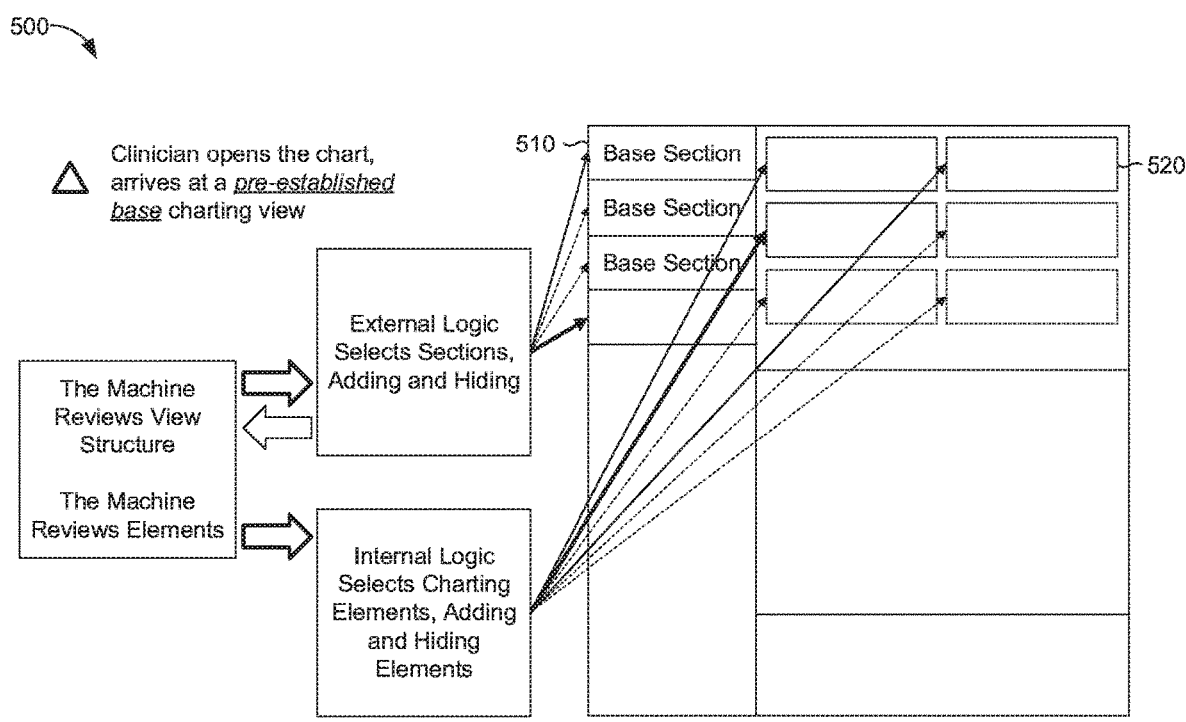
FIG. 5 depicts an illustrative screen display of a pre-established base charting view enhanced with contextual triggers and dynamic content retrieval from the charting library, in accordance with embodiments of the present invention.
Figure 6:
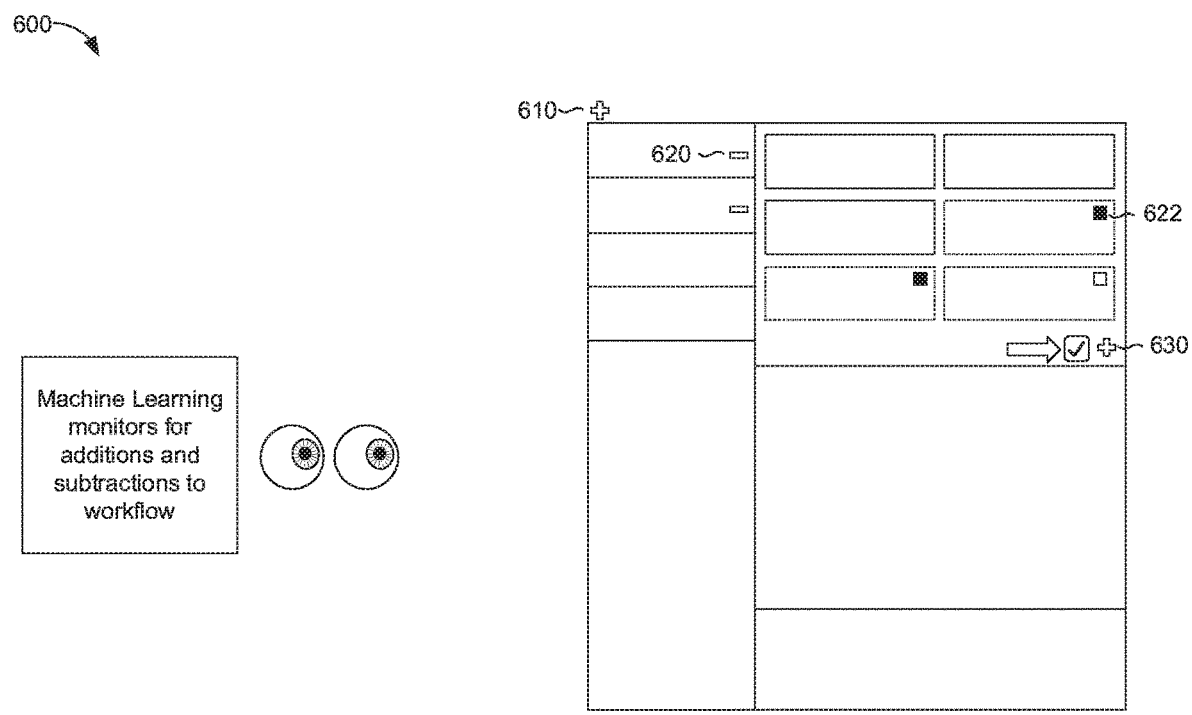
FIG. 6 depicts an illustrative screen display of user customizations and according machine learning and contextual awareness in terms of the pre-established base charting view, in accordance with embodiments of the present invention.
Figure 7:
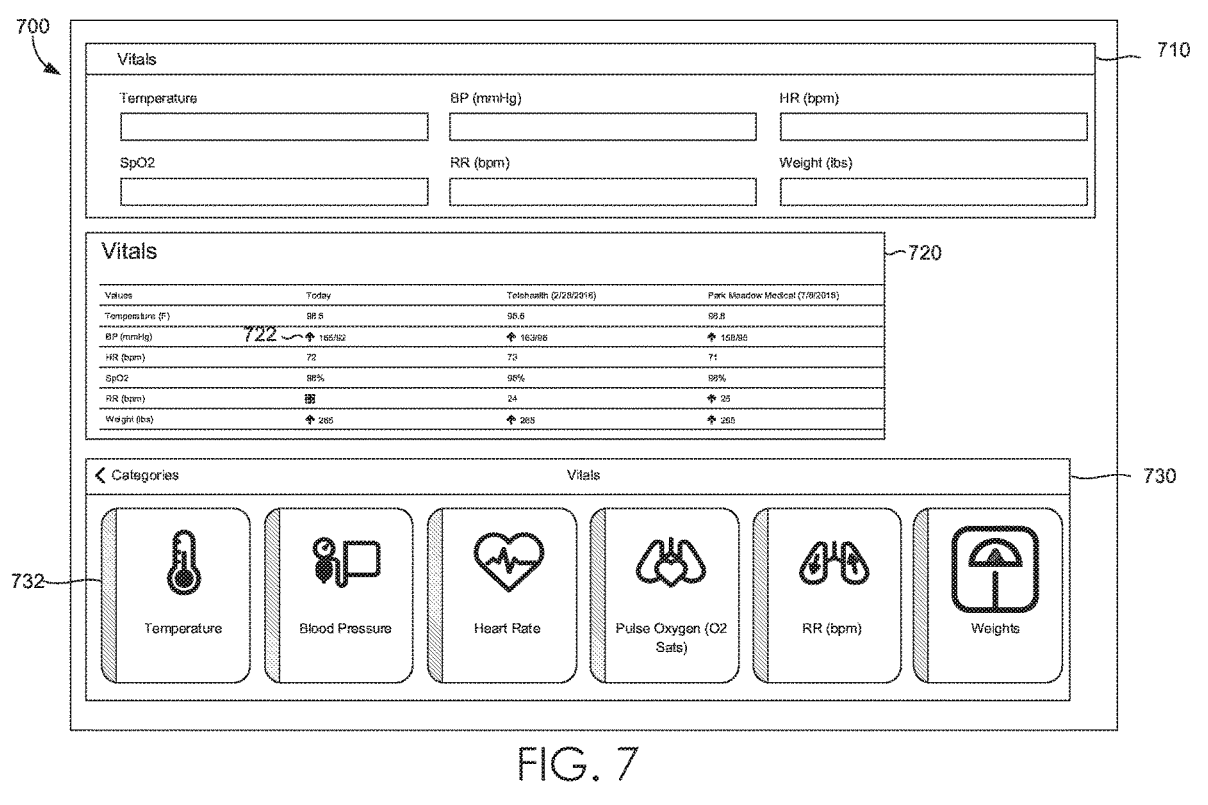

With reference to FIGS. 5-7, illustrative screen displays 500 and 600 of embodiments of the present invention are shown. It is understood that each of the illustrative screen displays are connected logically, such that they comprise a user interface designed for providing integrated charting. The screen displays may appear in any order and with any number of screen displays, without regard to whether the screen display is described or depicted herein. The screen displays provide tools that enable higher quality, consistency, and efficiency during the curation process, in accordance with embodiments of the present invention.

Referring initially, to FIG. 5, an illustrative screen display of a pre-established base charting view 500, in accordance with embodiments of the present invention. Initially, the pre-established base charting view 500 is presented when a clinician opens a chart. The pre-established base charting view 500 includes the structure of the workflow recommendation that is common to all clients. The structure itself, each base section, and each charting section may each be associated with a model code. External logic selects one or more base sections 510 to add or hide. The external logic may correspond to a workflow recommendation comprising model concepts. For example, previously utilized base sections, a diagnosis, demographics of the patient, role of the clinician, unit of health care facility, type of health care facility may all be factors the external logic sorts through to determine which of the one or more base sections 510 to add or hide. Internal logic selects one or more charting elements 520 to add or hide. The internal logic may correspond to a specific workflow recommendation comprising client domain specific customized concepts. For example, previously utilized charting sections or learned preferences of the health care facility, unit of the health care facility, or the clinician may all be factors the internal logic sorts through to determine which of the one or more charting elements 520 to add or hide.

In FIG. 6, an illustrative screen display 600 of user customizations to the pre-established base charting view, in accordance with embodiments of the present invention. In this illustration, the base charting view 600 is illustrated. As the clinician makes additions or subtractions to the workflow, such as by clicking the addition 610 or subtraction buttons 620, the system utilizes machine learning to monitor the preferences of the user. These preferences may be contributing factors to the internal logic or external logic described with respect to FIG. 5. Additionally, when the user is satisfied with the updated structure, the user can click the populate button 630 to prepopulate the selected charting elements 622 with prepopulated data, as illustrated in FIG. 7.

FIG. 7 is an illustrative screen display of a pre-established base charting view with prepopulated data 700, in accordance with embodiments of the invention. As shown, the selections made by the user correspond to vitals and include temperature, blood pressure, heart rate, pulse oxygen, respiratory rate, and weight. A charting section 710 enables the user to chart vitals for the patient. When data is entered, the model codes are mapped to client codes corresponding to the data, and the data can be pushed to an electronic medical record of the patient for the client. Because a model code exists for each of the charting elements, the system is able to populate a history section 720 previous data that was charted for a specific encounter for that ontology. Additional data may be available for each charting element provided by the history section 720 as indicated by an arrow 722. Attributes of the charting elements may be further configured by selecting the appropriate button in the categories section 730. For example, the temperature button 732 may enable the user to select whether the temperature is oral, rectal, body, and the like.

Figure 8:
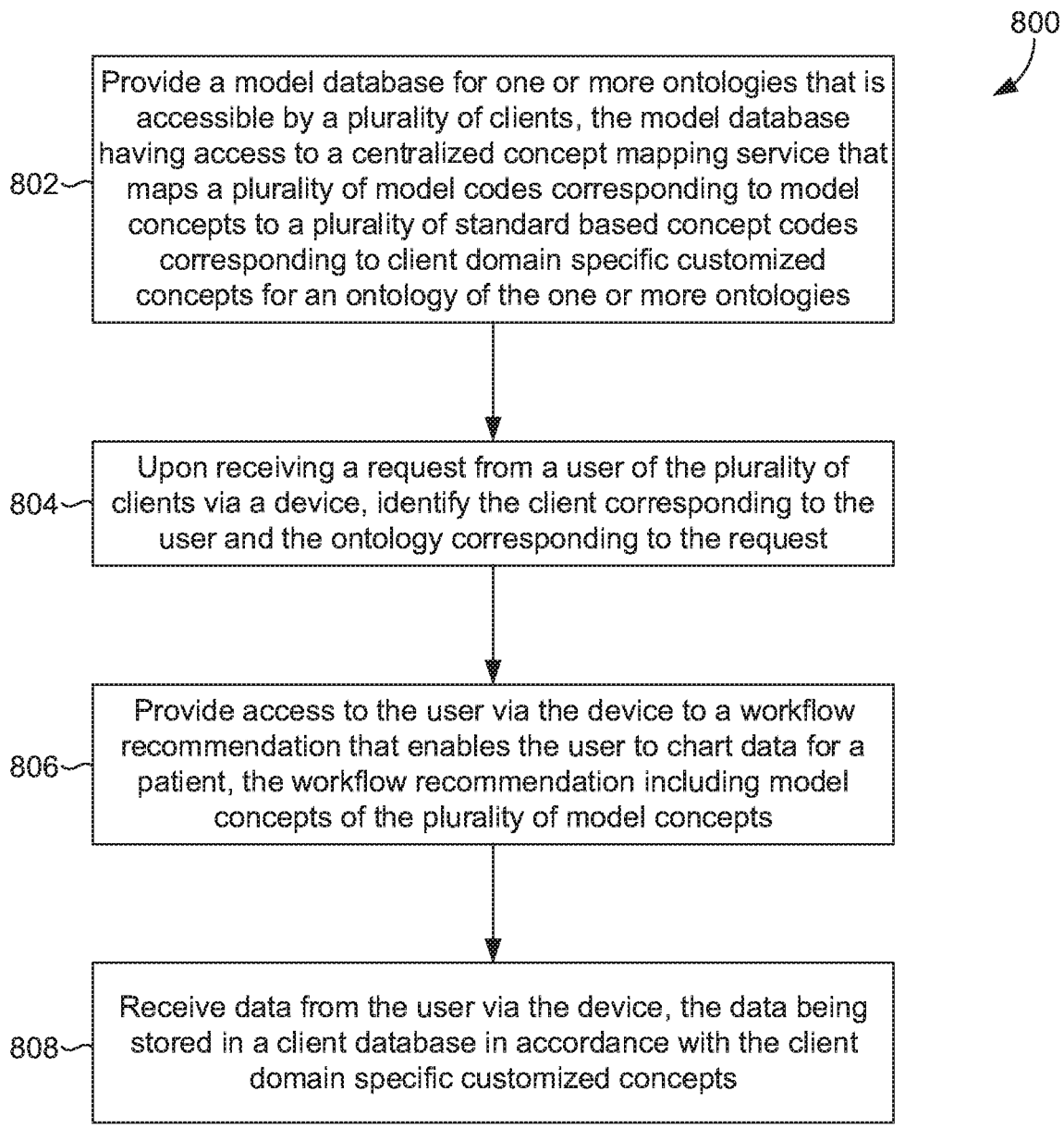
FIG. 8 depicts a flow diagram of a method for providing a device-agnostic workflow recommendation, in accordance with an embodiment of the present invention.

Turning now to FIG. 8, a flow diagram is provided illustrating a method 800 for providing a workflow recommendation, in accordance with embodiments of the present invention. Method 800 may be performed by any computing device (such as computing device described with respect to FIG. 1) with access to a cloud-based integrated charting system (such as the one described with respect to FIGS. 2-4) or by one or more components of the cloud-based integrated charting system.

Initially, at step 802, a model database is provided for one or more ontologies that is accessible by a plurality of clients. The model database has access to a centralized concept mapping service that maps a plurality of model codes corresponding to the model database for an ontology of the one or more ontologies to a plurality of standard based concept codes corresponding to one or more client databases of a client of the plurality of clients.

At step 804, upon receiving a request from a user of the plurality of clients via a device, the client corresponding to the user and the ontology corresponding to the request is identified.

At step 806, access to the user is provided via the device to a workflow recommendation that enables the user to chart data for a patient. The workflow recommendation includes model concepts of the plurality of model concepts. The model concepts may include a series of questions and answers. Additionally, the workflow recommendation may be prepopulated with data from the client database of the one or more client databases.

At step 808, data is received from the user via the device. The data is stored in a client database of the one or more client databases in accordance with a client concept of the plurality of concepts. In some embodiments, stored data is provided to the user via the device. The stored data corresponds to client domain specific customized concepts of the plurality of client domain specific customized concepts that map to model concepts of the workflow recommendation.

In embodiments, the user is enabled to modify the workflow recommendation to generate a specific workflow recommendation by modifying the model concepts that are included in the workflow recommendation. A second client may be prompted to indicate if the workflow recommendation for the second client should include the modifications of the specific workflow recommendation.

In embodiments, a plurality of model concepts corresponding to the model database for an ontology of the one or more ontologies is mapped to a plurality of client domain specific customized concepts corresponding to one or more client databases of a client of the plurality of clients. A client concept of the plurality of client domain specific customized concepts may be mapped to more than one model concept of the plurality of model concepts.

In some embodiments, a neural network is trained to map the plurality of model concepts to the plurality of client domain specific customized concepts. During training, a terminologist may be prompted to confirm suggestions of the neural network. Once the neural network is trained, the trained neural network maps the plurality of model concepts to the plurality of client domain specific customized concepts.

In embodiments, the specific workflow recommendation, configuration data, and actual workflow usage corresponding to the workflow recommendation is stored in a build database. The actual workflow usage may be measured inside the specific workflow recommendation and across applications utilizing the specific workflow recommendation. Optimal workflow usage may be stored in a workflow database. The optimal workflow usage may be measured inside the workflow recommendation and across applications utilizing the workflow recommendation.

In embodiments, KPI data may be identified and/or stored in a KPI database. The KPI data compares the workflow usage to the actual workflow usage. The centralized concept mapping service utilizes the KPI data to make modifications to the workflow recommendation or to the model concepts. Additionally or alternatively, the KPI data may be utilized to measure clinical outcomes, client outcomes, or distributed value as it relates to the workflow recommendation or the specific workflow recommendation.

Figure 9:
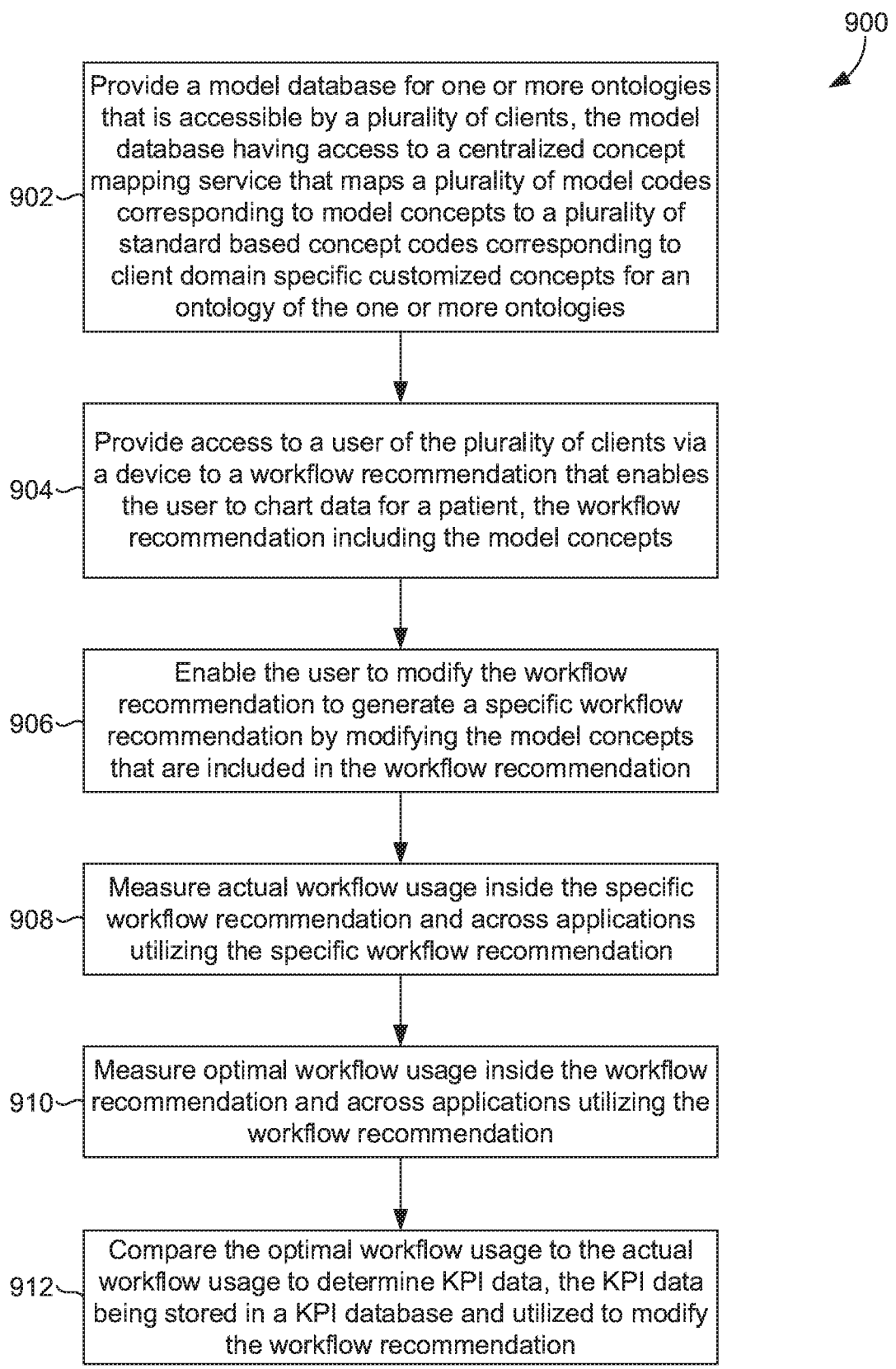
FIG. 9 depicts a flow diagram of a method for determining key performance indicator data for the workflow recommendation, in accordance with embodiments of the invention.

Turning now to FIG. 9, a flow diagram is provided illustrating a method 900 for determining key performance indicator data for the workflow recommendation, in accordance with embodiments of the present invention. Method 900 may be performed by any computing device (such as computing device described with respect to FIG. 1) with access to a cloud-based integrated charting system (such as the one described with respect to FIGS. 2-4) or by one or more components of the cloud-based integrated charting system.

Initially, at step 902, a model database is provided for one or more ontologies that is accessible by a plurality of clients. The model database has access to a centralized concept mapping service that maps a plurality of model codes corresponding to the model database for an ontology of the one or more ontologies to a plurality of standard based concept codes corresponding to one or more client databases of a client of the plurality of clients.

At step 904, access is provided to a user of the plurality of clients via a device to a workflow recommendation that enables the user to chart data for a patient. The workflow recommendation includes model concepts of the plurality of model concepts.

At step 906, the user is enabled to modify the workflow recommendation to generate a specific workflow recommendation by modifying the model concepts that are included in the workflow recommendation.

At step 908, actual workflow usage inside the specific workflow recommendation and across applications is measured utilizing the specific workflow recommendation. The specific workflow recommendation, configuration data, and the actual workflow usage corresponding to the workflow recommendation may be stored in a build database.

At step 910, optimal workflow usage inside the workflow recommendation and across applications is measured utilizing the workflow recommendation. The optimal workflow usage is stored in a workflow database.

At step 912, the workflow usage is compared to the actual workflow usage to determine KPI data. The KPI data may be stored in a KPI database and can be utilized to modify the workflow recommendation.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more computer storage media having computer-executable instructions embodied thereon that, when executed by a computer, causes the computer to perform operations for managing workflow recommendations across a plurality of clients, the operations comprising:

providing, by a cloud-based integrated charting system that utilizes a centralized concept mapping service across services and a plurality of clients to provide insights for a provider into customizations made by the plurality of clients, a model database for one or more ontologies that is accessible by the plurality of clients, the model database having access to the centralized concept mapping service that maps a plurality of model codes corresponding to charting elements to a plurality of standard based concept codes corresponding to client domain specific customized concepts for an ontology of the one or more ontologies;

responsive to receiving, by the cloud-based integrated charting system, a request from a user corresponding to a client of the plurality of clients via a device: identifying the client corresponding to the user and the ontology corresponding to the request;

providing, by the cloud-based integrated charting system, access to the user via the device to a recommended workflow that enables the user to chart data for a patient, the recommended workflow including the charting elements;

receiving, by the cloud-based integrated charting system, data from the user via the device, the data being stored in a client database in accordance with the client domain specific customized concepts;

enabling, by the cloud-based integrated charting system, the user to modify the recommended workflow to generate a user-modified workflow by modifying one or more of the charting elements that are included in the recommended workflow;

generating, by the cloud-based integrated charting system, key performance indicator (KPI) data based at least on a comparison of recorded usage of the recommended workflow with recorded usage of the user-modified workflow;

determining, by the cloud-based integrated charting system based at least on the KPI data, that the user-modified workflow performs better with respect to one or more of clinical outcomes, client outcomes, or distributed value than the recommended workflow for at least one charting element;

responsive to determining that the user-modified workflow performs better than the recommended workflow for at least one charting element: generating, by the cloud-based integrated charting system, one or more modifications to one or more charting elements included the recommended workflow for future workflow recommendations;

prompting, by the cloud-based integrated charting system, a second client of the plurality of clients to indicate if the recommended workflow for the second client should include the one or more modifications to the one or more charting elements included in the recommended workflow.

2. The media of claim 1, further comprising providing stored data to the user via the device, the stored data corresponding to client domain specific customized concepts of the plurality of client domain specific customized concepts that map to charting elements of the recommended workflow.

3. The media of claim 1, wherein the recommended workflow is prepopulated with data from the client database of one or more client databases.

4. The media of claim 1, further comprising associating the charting elements to a series of questions and answers.

5. The media of claim 1, further comprising mapping a plurality of charting elements corresponding to the model database for an ontology of the one or more ontologies to a plurality of client domain specific customized concepts corresponding to one or more client databases of a client of the plurality of clients.

6. The media of claim 5, wherein a client concept of the plurality of client domain specific customized concepts is mapped to more than one charting element of the plurality of charting elements.

7. The media of claim 1, further comprising training a neural network to map the plurality of charting elements to the plurality of client domain specific customized concepts.

8. The media of claim 7, further comprising prompting a terminologist to confirm suggestions of the neural network.

9. The media of claim 8, further comprising utilizing the trained neural network to map the plurality of charting elements to the plurality of client domain specific customized concepts.

10. The media of claim 1, further comprising storing the specific user-modified workflow, configuration data, and the recorded usage of the user-modified workflow in a build database, the recorded usage of the user-modified workflow usage being measured inside the user-modified workflow and across applications utilizing the user-modified workflow.

11. The media of claim 10, further comprising storing the recorded usage of the recommended workflow in a workflow database, the recorded usage of the recommended workflow being measured inside the recommended workflow and across applications utilizing the recommended workflow.

12. A computerized method for determining key performance indicator (KPI) data for workflow usage across a plurality of clients, the method comprising:
providing, by a cloud-based integrated charting system that utilizes a centralized concept mapping service across services and a plurality of clients to provide insights for a provider into customizations made by the plurality of clients, a model database for one or more ontologies that is accessible by the plurality of clients, the model database having access to the centralized concept mapping service that maps a plurality of model codes corresponding to charting elements to a plurality of standard based concept codes corresponding to client domain specific customized concepts for an ontology of the one or more ontologies;
responsive to receiving, by the cloud-based integrated charting system, a request from a user corresponding to a client of the plurality of clients via a device: identifying the client corresponding to the user and the ontology corresponding to the request;
providing, by the cloud-based integrated charting system, access to the user via the device to a recommended workflow that enables the user to chart data for a patient, the recommended workflow including the charting elements;
receiving, by the cloud-based integrated charting system, data from the user via the device, the data being stored in a client database in accordance with the client domain specific customized concepts;
enabling, by the cloud-based integrated charting system, the user to modify the recommended workflow to generate a user-modified workflow by modifying one or more of the charting elements that are included in the recommended workflow;
generating, by the cloud-based integrated charting system, key performance indicator (KPI) data based at least on a comparison of recorded usage of the recommended workflow with recorded usage of the user-modified workflow;
determining, by the cloud-based integrated charting system based at least on the KPI data, that the user-modified workflow performs better with respect to one or more of clinical outcomes, client outcomes, or distributed value than the recommended workflow for at least one charting element;
responsive to determining that the user-modified workflow performs better than the recommended workflow for at least one charting element: generating, by the cloud-based integrated charting system, one or more modifications to one or more charting elements included the recommended workflow for future workflow recommendations;
prompting, by the cloud-based integrated charting system, a second client of the plurality of clients to indicate if the recommended workflow for the second client should include the one or more modifications to the one or more charting elements included in the recommended workflow.

13. The method of claim 12, further comprising storing the user-modified workflow, configuration data, and the recorded usage of the user-modified workflow in a build database.

14. The method of claim 13, further comprising storing the recorded usage of the recommended workflow in a workflow database.

15. A system for managing workflow recommendations across a plurality of clients, the system comprising:
a processor; and
a computer storage medium storing computer-usable instructions that, when used by the processor, cause the processor to perform operations comprising:
providing, by a cloud-based integrated charting system that utilizes a centralized concept mapping service across services and a plurality of clients to provide insights for a provider into customizations made by the plurality of clients, a model database for one or more ontologies that is accessible by the plurality of clients, the model database having access to the centralized concept mapping service that maps a plurality of model codes corresponding to charting elements to a plurality of standard based concept codes corresponding to client domain specific customized concepts for an ontology of the one or more ontologies;
responsive to receiving, by the cloud-based integrated charting system, a request from a user corresponding to a client of the plurality of clients via a device: identifying the client corresponding to the user and the ontology corresponding to the request;
providing, by the cloud-based integrated charting system, access to the user via the device to a recommended workflow that enables the user to chart data for a patient, the recommended workflow including the charting elements;
receiving, by the cloud-based integrated charting system, data from the user via the device, the data being stored in a client database in accordance with the client domain specific customized concepts;
enabling, by the cloud-based integrated charting system, the user to modify the recommended workflow to generate a user-modified workflow by modifying one or more of the charting elements that are included in the recommended workflow;
generating, by the cloud-based integrated charting system, key performance indicator (KPI) data based at least on a comparison of recorded usage of the recommended workflow with recorded usage of the user-modified workflow;
determining, by the cloud-based integrated charting system based at least on the KPI data, that the user-modified workflow performs better with respect to one or more of clinical outcomes, client outcomes, or distributed value than the recommended workflow for at least one charting element;
responsive to determining that the user-modified workflow performs better than the recommended workflow for at least one charting element: generating, by the cloud-based integrated charting system, one or more modifications to one or more charting elements included the recommended workflow for future workflow recommendations;

prompting, by the cloud-based integrated charting system, a second client of the plurality of clients to indicate if the recommended workflow for the second client should include the one or more modifications to the one or more charting elements included in the recommended workflow.

\* \* \* \* \*